United States Patent
Metzger

(10) Patent No.: US 6,410,236 B1
(45) Date of Patent: Jun. 25, 2002

(54) CORRECTING DIASTOLIC DYSFUNCTION IN HEART FAILURE

(75) Inventor: Joseph M. Metzger, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 09/387,919

(22) Filed: Sep. 1, 1999

(51) Int. Cl.[7] .............................................. C12Q 1/68

(52) U.S. Cl. ........................................................ 435/6

(58) Field of Search ............................................ 435/6

(56) References Cited

U.S. PATENT DOCUMENTS

| | | |
|---|---|---|
| 5,139,941 A | 8/1992 | Muzyczka et al. |
| 5,173,414 A | 12/1992 | Lebkowski et al. |
| 5,676,954 A | 10/1997 | Brigham |
| 5,843,742 A | 12/1998 | Natsoulis et al. |
| 5,908,777 A | 6/1999 | Lee et al. |

FOREIGN PATENT DOCUMENTS

| | | |
|---|---|---|
| WO | WO 92/01070 | 1/1992 |
| WO | WO 93/03769 | 3/1993 |

OTHER PUBLICATIONS

Anderson and Young, Quantitative Filter Hybridization, in *Nucleic Acid Hybridization* (1985).
Baylor and Hollingworth, "Model of Sarcomeric $Ca^{2+}$ Movements, Including ATP $Ca^{2+}$ Binding and Diffustion, during Activation of frog Skeletal Muscle", J. Gen. Physiol 112:297–316 (1988).
Becker et al. Use of Recombinant Adenovirus for Metabolic Engineering of Mammalian Cells, in *Methods in cell Biology*, vol. 43, M.G. Roth, ed., Academic Press, NY (1994).
Cannell et al., "Spatial non–Uniformities in $[Ca^{2+}]_i$ during Excitation–Contraction coupling in cardiac Myocytes," Biophs. J. 67:1942–1956 (1994).
Carter, "Adeno–associated virus vectors," Curr. Opin. Biotech. 3:533–539 (1992).
Felgner et al., "Cationic liposome–mediated transfection," Nature 337:387–388 (1989).
Felgner et al., "Lipofection: A highly efficient, lipid–mediated DNA–transfection procedure" Proc. Nat. Acad. Sci. (1987) 84:7413–7416 (1987).
Ferrari et al., "New developments in the generation of Ad–free, high–titer rAAV gene therapy vectors," Nature Med. 3(11):1295–1297 (1997).
Fohr et al., "Human α and β parvalbumins: Sturcture and tissue–specific expression," Eur. J. Biochem. 21593:719–727 (1993).
Gheorghiade et al., "Current medical therapy for advanced heart failure," Am. Heart. J. 135:S231–S248 (1998).
Graham and Prevec, Manipulation of Adenovirus Vectors, in *Gene Transfer and Expression Protocols*, E.J. Murray ed., Humana, Clifton, NJ (1991).
Graham and van der Eb, "A New Technique for the Assay of Infectivity of Human Adenovirus 5 DNA," Virol., 52:456 (1973).
Grossman, "Diastolic Dysfunction and Congestive Heart Failure," Circulation 81 (Suppl. III):1–7 (1990).
Hou et al., "Parvalbumin content and $Ca^{2+}$ and $Mg^{2+}$ dissociation rates correlated with changes inrelaxation rate of frog muscle fibres," J. Physiol. 441:285–304 (1992).
Hug and Sleight, "Liposomes for the transformation of eukaryotic cells," Biochem. Biophys. Acta. 1097:1–17 (1991).
Kotin, "Prospects for the Use of Adeno–Associated Virus as a Vector for Human Gene Therapy," Human Gene Ther. 5:793–801 (1994).
Lännergren et al., "Force relaxation, labile heat and parvalbumin content of skeletal muscle fires of *Xenopus laevis*," J. Physiol. 463:123–140 (1993).
Lebkowski et al., "Adeno–Associated Virus: a Vector System for Efficient Introduction Integration of DNA into a Variety of Mammalian Cell Types," Mol. Cell. Biol. 8:3988–3996 (1988).
Levit et al., "National health expenditures, 1990," Health Care Finan. Rev. 13:29–54 (1991).
Lorell, "Significance of diastolic dysrfunction of the heart," Annu. Rev. Med.42:411–436 (1991).
Morgan, "Abnormal intracellular modulation of calcium as a major cause of cardiac contractile dysfunction," New. Engl. J.Med. 325:625 (1991).
Müntener et al., "Increase of skeletal muscle relaxation speed by direct injection of parvalbumin cDNA," Proc. Nat. Acad. Sci. 92:6504–6508 (1995).
Muzyczka, "Use of Adeno–Associated Virus as a General Transductio Vector for Mammalian Cells," Curr. Top. Microbiol. Immunol. 158:97–129 (1994).
O'Connell, "Economic Impact of Heart Failure in the United States: Time for a Different Approach," J. Heart Lung Transplant 13:S107–S248 (1994).
Palermo et al., "Transgenic Remodeling of the contractile Apparatus in the Mammalian Heart," Circul. Res. 78:(3)504–509 (1996).

(List continued on next page.)

Primary Examiner—Deborah J. R. Clark
Assistant Examiner—Peter Brunovskis
(74) Attorney, Agent, or Firm—Medlen & Carroll, LLP

(57) ABSTRACT

The present invention relates to the overexpression of a calcium binding protein in cardiac myocytes in vivo and in vitro, and in particular, to the correction of diastolic dysfunction. Expression of the calcium binding protein parvalbumin in cardiac myocytes results in an increase in the rate of relaxation of the cardiac myocyte, in vivo and in vitro. The parvalbumin is expressed from an adenovirus vector, adeno-associated virus vector, or gutted adenovirus vector. The transfected in vivo and in vitro cardiac myocytes are also useful in drug screens.

3 Claims, 9 Drawing Sheets

OTHER PUBLICATIONS

Sambrook et al., *Molecular Cloning: A Laboratory Manual*, Cold Spring Harbor Press, NY, pp. 7.39–7.52, 9.31–9.58, (1989).

Shelling and Smith, "Targeted integration of transfected and infected adeno–associated virus vectors containing the neomycin resistance gene," Gene Ther. 1:165–169 (1994).

Straubinger et al., "Liposomes as Carriers for Intracellular Delivery of Nucleic Acids," Meth. Enzym. 101:512–527 (1993).

Westfall et al., "Adenovirus–Mediated Myofilament Gene Transfer into Adult Cardiac Myocytes," Meth. Cell. Biol. 32:307–322 (1998).

Zhou et al., J. Exp. Med. 179:1867–1875 (1994).

Arai et al., "Sarcoplasmic Reticulum Gene Expression in Cardiac Hypertrophy and Heart Failure," Circ. Res. 74:555–564 (1994).

Chen and Chien, "Complexity in simplicity: monogenic disorders and complex cardiomyopathies," J. Clin. Invest. 103:1483–1485 (1999).

Gomez et al., "Defective excitation–Contraction Coupling in Experimental cardiac Hypertrophy and Heart Failure," Science 276:800–806 (1997).

Grimm and Kleinschmidt, "Progress in Adeno–Associated Virus Type 2 Vector Production: Promises and Prospects for Clinical Use," Hum. Gene Ther. 10:2445–1450 (1999).

Gwathmey et al., "Abnormal Intracellular Calcium Handling in Myocardium From Patients With End–Stage Heart Failure," Circ. Res. 61:70–76 (1987).

Katz, "Is the Failing Heart an Energy–starved Organ?" J. of Cardiac Failure 2:267–272 (1996).

Hasenfuss, "Calcium Pump Overexpression and Myocardial Function: Implications for Gene Therapy of Myocardial Failure," Circ. Res. 83:966–968 (1998).

Hess et al., "Diastolic Function and Myocardial Structure in Patients with Myocardial Hypertrophy," Circ. 63:360–371 (1981).

Hunter and Chien, "Signaling Pathways for Cardiac Hypertrophy and Failure," New Engl. J. Med.341:1276–1283 (1999).

Loukianov et al., "Enhanced Myocardial contractility and Increased $Ca^{2+}$ Transport Function in Transgenic Hearts Expressing the Fast–Twitch Skeletal Muscle Sarcoplasmic Reticulum Ca2+–ATPase," Circ. Res. 83:889–897 (1998).

Morgan et al., "Abnormal Intracellular Calcium Handling, a Major Cause of Systolic and Diastolic Dysfunction in Ventricular Myocardium From Patients with Heart Failure," Circ. 81 (suppl. III):III–21–III–32 (1990).

Nihoyannopoulos et al., "diastolic Function in Hypertrophic Cardiomyopathy: Relation to Exercise Capacity," J. Amer. Coll. Card. 19:536–540 (1992).

Vasan et al., "Congestive Heart Failure With Normal Left Ventricular Systolic Function," Arch. Intern. Med. 156:146–157 (1996).

SEQ ID NO:1 Human parvalbumin cDNA:

```
  1 accagcccag cctttcagtg caggctccag ccctccaccc ccacccgagt tgcaggatgt
 61 cgatgacaga cttgctgaac gctgaggaca ggtgggagcc tttagcgcta
121 ccgactcctt cgaccacaaa agttcttcc tcaagaaggc cctgaagaaa aagagtgcgg
181 atgatgtgaa gaagtgttt cacatgctgg acaaggacaa aagtggcttc atcgaggagg
241 atgagctggg attcatccta aaaggcttct cccagatgc cagagacctg tctgctaaag
301 aaaccaagat gctgatggct gctggagaca aagatggggga cggcaaaatt ggggttgacg
361 aattctccac tctggtggct gaaagctaag aagcactgac tgccctggt cttccacctc
421 tctg
```

SEQ ID NO:2 Mouse parvalbumin cDNA:

```
  1 gaattctcca ctctggtggc tgaaagctaa gtggcgctga ctgcttgggt ccccaccc
 61 tccatcccca acgcccatc tcagcccctt cgcggcccct cctgagtttc tgttcagttt
121 gtttgtgtta ttttttactc ccccatcctc tatgacgcc ggatgacgcc attcttctgg
181 aaatgctgga gaaacaataa aggctgtacc aatctgtacc cacctgtagg gaggacccag
241 gcctggcagg gtgttggttt ggcaagtttt ttctttct tttagggca gtggggtat
301 agtagaaaaa gtgagataag tcaaaggaca acgccccgat atctcctgcc tgcttggtac
361 tgagtgctca tgtgggtcac ctcgttcaat ctctgcacct ttcccacaag gagatgggg
421 tgatggatcg tccatcttaa agatacagaa actgcctttt aaagagcaga agggaaggga
481 aggggttgagt cctttcaggac tagctagatc aaaggactcc aatgacactc tatcaattgc
541 ttttgacttt gctgtgataa aatacctgaa aaga
```

FIG. 8A

SEQ ID NO:3 Rat parvalbumin cDNA:

```
  1 ttttttttt ttttttccg atgggtacag cctttattgt ttctccagca ttttccagaa
 61 gagtggtgtc attcgagggc cataaaggat gggggagtaa aaaataacat aaacaaactg
121 aacagaaacc caggaggggcc gcgagaaggg ctgagatggg gcatgggggg tggagaggtg
181 ggagacccaa gcagtcagcg ccacttagct ttcggccacc agagtggaga attcttcaac
241 cccaatcttg ccgtccccgt ccttgtctcc agcagccatc agcgtctttg ttttccttagc
301 agacaagtct ctgcatctg aggagaagcc cttcagaatg gacccagct catcctcctc
361 aatgaagcca cttttgtctt tgtccagaat gtggaacacc ttcttcacat catccgcact
421 ctttttcttc aggcccacca tctggaagaa cttttgtgg tcgaaggagt ctgcagcagt
481 aaaggctcct atcgccttct tgatgtcctc agcgctgagc aagtctgtca tcgacatcct
541 gca
```

FIG. 8B

SEQUENCE LISTING

```
<160> NUMBER OF SEQ ID NOS:  6

<210> SEQ ID NO 1
<211> LENGTH: 424
<212> TYPE: DNA
<213> ORGANISM: Homo sapiens

<400> SEQUENCE: 1
accagcccag cctttcagtg caggctccag ccctccaccc ccacccgagt tgcaggatgt     60
cgatgacaga cttgctgaac gctgaggaca tcaagaaggc ggtgggagcc tttagcgcta    120
ccgactcctt cgaccacaaa aagttcttcc aaatggtcgg cctgaagaaa aagagtgcgg    180
atgatgtgaa gaaggtgttt cacatgctgg acaaggacaa aagtggcttc atcgaggagg    240
atgagctggg attcatccta aaaggcttct ccccagatgc cagagacctg tctgctaaag    300
aaaccaagat gctgatggct gctggagaca aagatgggga cggcaaaatt ggggttgacg    360
aattctccac tctggtggct gaaagctaag aagcactgac tgcccctggt cttccacctc    420
tctg                                                                424

<210> SEQ ID NO 2
<211> LENGTH: 574
<212> TYPE: DNA
<213> ORGANISM: Mus musculus

<400> SEQUENCE: 2
gaattctcca ctctggtggc tgaaagctaa gtggcgctga ctgcttgggt cccccacctc     60
tccatcccca acgccccatc tcagcccttc tcgcggccct cctgagtttc tgttcagttt    120
gtttgtgtta tttttactc ccccatcctc tatggccctc ggatgacgcc attcttctgg    180
aaatgctgga gaaacaataa aggctgtacc aatcggacac cacctgtagg gaggacccag    240
gcctggcagg gtgttggttt ggcaagtttt ttttctttct ttttagggca gtggggtat     300 agtagaaaaa gtgagataag tcaaaggaca acgcccgat atctcctgcc tgcttggtac    360
tgagtgctca tgtgggtcac ctcgttcaat ctctgcacct ttcccacaag gagatggggg    420
```

```
tgatggatcg tccatcttaa agatacagaa actgccttt  aaagagcaga agggaaggga      480
agggttgagt ccttcaggac tagctagatc aaaggactcc aatgacactc tatcaattgc      540
ttttgacttt gctgtgataa aatacctgaa aaga                                  574
```

<210> SEQ ID NO 3
<211> LENGTH: 543
<212> TYPE: DNA
<213> ORGANISM: Rattus norvegicus

<400> SEQUENCE: 3

```
ttttttttt  ttttttccg  atgggtacag cctttattgt ttctccagca ttttccagaa       60
gagtggtgtc attcgagggc cataaaggat gggggagtaa aaataacat  aaacaaactg      120 aacagaaacc caggagggcc gcgagaaggg ctgagatggg gcatggggggg tggagaggtg      180 ggagacccaa gcagtcagcg ccacttagct ttcggccacc agagtggaga attcttcaac      240
cccaatcttg ccgtccccgt ccttgtctcc agcagccatc agcgtctttg tttccttagc      300
agacaagtct ctggcatctg aggagaagcc cttcagaatg acccagct  catcctcctc      360 aatgaagcca cttttgtctt tgtccagaat gtggaacacc ttcttcacat catccgcact      420 cttttcttc  aggcccacca tctggaagaa cttttgtgg  tcgaaggagt ctgcagcagt      480
aaaggctcct atcgccttct tgatgtcctc agcgctgagc aagtctgtca tcgacatcct      540
gca                                                                    543
```

<210> SEQ ID NO 4
<211> LENGTH: 110
<212> TYPE: PRT
<213> ORGANISM: Homo sapiens
<220> FEATURE:
<221> NAME/KEY: SITE
<222> LOCATION: (53)
<223> OTHER INFORMATION: Xaa at this position means any amino acid.
<221> NAME/KEY: SITE
<222> LOCATION: (98)
<223> OTHER INFORMATION: Xaa at this position means any amino acid.

<400> SEQUENCE: 4

```
Met Ser Met Thr Asp Leu Leu Asn Ala Glu Asp Ile Lys Lys Ala Val
 1               5                  10                  15

Gly Ala Phe Ser Ala Thr Asp Ser Phe Asp His Lys Lys Phe Phe Gln
            20                  25                  30

Met Val Gly Leu Lys Lys Lys Ser Ala Asp Val Lys Val Phe
        35                  40                  45

His Met Leu Asp Xaa Asp Lys Ser Gly Phe Ile Asx Glu Asp Glu Leu
    50                  55                  60

Gly Phe Ile Leu Lys Gly Phe Ser Pro Asp Ala Arg Asp Leu Ser Ala
65                  70                  75                  80

Lys Glu Thr Lys Met Leu Met Ala Ala Gly Asp Lys Asp Gly Asp Gly
                85                  90                  95

Lys Xaa Gly Val Asp Glu Phe Ser Thr Leu Val Ala Glu Ser
            100                 105                 110
```

<210> SEQ ID NO 5
<211> LENGTH: 110
<212> TYPE: PRT
<213> ORGANISM: Rattus norvegicus

<400> SEQUENCE: 5

```
Met Ser Met Thr Asp Leu Leu Ser Ala Asx Asp Ile Lys Lys Ala Ile
```

-continued

```
  1               5                    10                   15
Gly Ala Phe Thr Ala Ala Asp Ser Phe Asp His Lys Lys Phe Phe Gln
                20                  25                  30

Met Val Gly Leu Lys Lys Ser Ala Asp Val Lys Lys Val Phe
            35                  40                  45

His Ile Leu Asp Lys Asp Lys Ser Gly Phe Ile Glu Glu Asp Glu Leu
         50                  55                  60

Gly Ser Ile Leu Lys Gly Phe Ser Ser Asp Ala Arg Asp Leu Ser Ala
 65                  70                  75                  80

Lys Glu Thr Lys Thr Leu Met Ala Ala Gly Asp Lys Asp Gly Asp Gly
                 85                  90                  95

Lys Ile Gly Val Glu Glu Phe Ser Thr Leu Val Ala Glu Ser
             100                 105                 110

<210> SEQ ID NO 6
<211> LENGTH: 110
<212> TYPE: PRT
<213> ORGANISM: Mus musculus

<400> SEQUENCE: 6

Met Ser Met Thr Asp Val Leu Ser Ala Asx Asp Ile Lys Lys Ala Ile
 1               5                  10                  15

Gly Ala Phe Ala Ala Asp Ser Phe Asp His Lys Lys Phe Phe Gln
                20                  25                  30

Met Val Gly Leu Lys Lys Asn Pro Asp Glu Val Lys Lys Val Phe
            35                  40                  45

His Ile Leu Asp Lys Asp Lys Ser Gly Phe Ile Glu Glu Asp Glu Leu
         50                  55                  60

Gly Ser Ile Leu Lys Gly Phe Ser Ser Asp Ala Arg Asp Leu Ser Ala
 65                  70                  75                  80

Lys Glu Thr Lys Thr Leu Leu Ala Ala Gly Asp Lys Asp Gly Asp Gly
                 85                  90                  95

Lys Ile Gly Val Glu Glu Phe Ser Thr Leu Val Ala Glu Thr
             100                 105                 110
```

CORRECTING DIASTOLIC DYSFUNCTION IN HEART FAILURE

This invention was made with Government support under a National Institutes of Health grant awarded by contract AG15434. The government has certain rights in this invention.

FIELD OF THE INVENTION

The present invention relates to the overexpression of a calcium binding protein in cardiac myocytes in vivo and in vitro, and in particular, to the correction of diastolic dysfunction.

BACKGROUND OF THE INVENTION

A strange irony of the remarkable advances in clinical cardiology over the last two decades is that it has lead to the emergence of an entirely new population of patients with advanced cardiovascular disease, termed, "heart failure." One characteristic of heart failure is a prolongation of the time course of the intracellular calcium transient that governs the duration of the contraction/relaxation cycle in heart muscle (Morgan, New Engl. J. Med. 325:625, [1991]). In diastolic dysfunction, the heart muscle fails to relax properly between beats, leading to an increased stiffness of the heart during diastole, and thereby generating excessive resistance of the heart chamber to refilling. In its simplest terms, diastolic dysfunction translates to the reduced ability of the heart to fill with blood (Gaasch and Le Winter (Eds.), *Left Ventricular Diastolic Dysfunction and Heart Failure*, Lea and Febiger, Philadelphia, Pa. [1993]).

In about 40% of patients diagnosed with heart failure, diastolic dysfunction is recognized as the primary pathophysiological mechanism precipitating the disease (Lorell, Annu. Rev. Med. 42: 411–36, [1991]). Diastolic dysfunction is also implicated in several other important disease states including hypertension, hypertrophic cardiomyopathy, diabetes-mediated heart disease, and is also a feature of the aging population in this country (Gaasch, supra). The incidence of heart failure in the United States is estimated to be 4–5 million individuals, with annualized hospital and care costs of about $12, billion per year (Levit et al., Health Care Finan. Rev. 13: 29–54, [1991]; O'Connell, J. Heart Lung Transplant 13: S107–S248, [1994]; Gheorghiade et al., Am. Heart J. 135: S231–S248, [1998]). Clearly, an understanding of the mechanisms of diastolic dysfuction, and the development of effective treatments for this disease, are of tremendous clinical importance.

To date there have been no effective drugs, chemicals or genetic interventions to directly treat diastolic dysfunction in patients. Traditional therapy, which is generally directed at improving systolic performance, is not applicable to treating diastolic dysfunction. No reason exists to administer digitalis, and arterial vasodilators may produce hypotension. Some patients may respond to a combination of beta adrenergic blocking agents and calcium channel blockers. However, these drugs act indirectly by slowing the heart rate. They do not directly act to increase the myocardial relaxation rate.

What is needed in the art are agents and methods for lessening the symptoms of diastolic dysfunction. Preferably, such agents would not have significant side effects such as causing hypotension.

SUMMARY OF THE INVENTION

The present invention relates to the overexpression of a calcium binding protein in cardiac myocytes in vivo and in vitro, and in particular, to the correction of diastolic dysfunction.

In some embodiments of the present invention, a vector comprising a nucleic acid encoding a calcium binding protein is provided. The present invention is not limited to a particular vector. Indeed, a variety of vectors are contemplated. In some embodiments, the vector is preferably an adenovirus vector. In other embodiments, the vector is preferably an adeno-associated virus vector. In still further embodiments, the vector is a gutted adenovirus vector which contains no adenovirus transcriptional elements.

The present invention is not limited to vectors comprising a nucleic acid encoding a particular calcium binding protein. Indeed, a variety of calcium binding proteins are contemplated. In some embodiments, the calcium binding protein is a member of the EF-hand family of calcium binding proteins. In other embodiments, the nucleic acid encoding the calcium binding protein encodes human parvalbumin, mouse parvalbumin, or rat parvalbumin.

Accordingly, in some embodiments, the nucleic acid is selected from SEQ ID NO:1, SEQ ID NO:2, and SEQ ID NO:3. In other embodiments, the nucleic acid is selected from nucleic acids which hybridize to SEQ ID NO:1, SEQ ID NO:2, and SEQ ID NO:3 under conditions of low to high stringency.

In some embodiments of the present invention, a mammalian cardiac myocyte comprising a nucleic acid encoding an exogenous calcium binding protein is provided. The present invention is not limited to myocytes comprising a nucleic acid encoding a particular calcium binding protein. Indeed, a variety of calcium binding proteins are contemplated. In some embodiments, the calcium binding protein is a member of the EF-hand family of calcium binding proteins. In other embodiments, the nucleic acid encoding the calcium binding protein encodes human parvalbumin, mouse parvalbumin, or rat parvalbumin. Accordingly, in some embodiments, the nucleic acid is selected from SEQ ID NO:1, SEQ ID NO:2, and SEQ ID NO:3. In other embodiments, the nucleic acid is selected from nucleic acids which hybridize to SEQ ID NO:1, SEQ ID NO:2, and SEQ ID NO:3 under conditions of low to high stringency. Additionally, the present invention is not limited to a particular type of nucleic acid. In some embodiments, the nucleic acid is DNA, while in other embodiments, the nucleic acid is preferably RNA (e.g., mRNA derived from transcription of the DNA). In some preferred embodiments, the intracellular concentration (post-transfection) of the mRNA corresponding to the nucleic acid (e.g., human parvalbumin mRNA) and the protein translated from the mRNA (e.g., human parvalbumin) is greater than the intracellular concentration in wild type myocytes, which normally do not express detectable levels of parvalbumin.

The present invention is not limited to any particular mammalian cardiac myocyte. Indeed, a variety of mammalian cardiac myocytes are contemplated. In some embodiments, the myocytes are rat or mice myocytes, while in other embodiments, the myocytes are human myocytes. In other embodiments, the myocytes are in vitro cultured myocytes. In still other embodiments, the myocytes are in vivo myocytes forming cardiac tissue in a mammal, including humans.

The present invention is not limited by the location of the nucleic acid within the transfected myocyte. In some embodiments, the nucleic acid is incorporated into the genome of the host cell, while in other embodiments the nucleic acid is located in the cytoplasm or nucleoplasm of the host cell.

The mammalian cardiac myocytes comprising an exogenous nucleic acid encoding a calcium binding protein have a variety of uses. In some embodiments of the present invention, the cardiac myocytes are used in an in vitro drug screen. In some embodiments, the screening method comprises providing a drug and the transfected cardiac myocyte. In further embodiments, the cardiac myocyte is preferably exposed to a drug. In some embodiments, the rate of relaxation of the cardiac myocytes are assayed in vitro in the presence or absence of the drug. The drug screening method of the present invention is not limited to any particular mammalian cardiac myocyte. Indeed, a variety of mammalian cardiac myocytes are contemplated. In some embodiments, the myocytes are rat or mice myocytes, while in other embodiments, the myocytes are human myocytes. In other embodiments, the myocytes are in vitro cultured myocytes. In still other embodiments, the myocytes are in vivo myocytes forming the cardiac tissue in a mammal.

In other embodiments of the present invention, a method of treating heart failure due to diastolic dysfunction is provided. In some embodiments of the present invention, a patient suffering from heart failure due to diastolic dysfunction and a vector comprising an exogenous nucleic acid encoding a calcium binding protein are provided. In other embodiments of the present invention, the cardiac myocytes of the patients are transfected with the vector. In some preferred embodiments, the intracellular concentration (post transfection) of the calcium binding protein encoded by the nucleic acid is greater than in wild type myocytes. In some particularly preferred embodiments, the rate of relaxation of the transfected myocytes is increased as compared to wild type myocytes. In other preferred embodiments, the rate of isovolumic relaxation is increased.

This method of treating heart failure is not limited to any particular nucleic acid encoding a calcium binding protein. Indeed, a variety of calcium binding proteins are contemplated. In some embodiments, the calcium binding protein is a member of the EF-hand family of calcium binding proteins. In other embodiments, the nucleic acid encoding the calcium binding protein encodes human parvalbumin, mouse parvalbumin, or rat parvalbumin. Accordingly, in some embodiments, the nucleic acid is selected from SEQ ID NO:1, SEQ ID NO:2, and SEQ ID NO:3. In other embodiments, the nucleic acid is selected from nucleic acids which hybridize to SEQ ID NO:1, SEQ ID NO:2, and SEQ ID NO:3 under conditions of low to high stringency.

Likewise, this method of treating heart failure is not limited to any particular vector. Indeed, a variety of vectors are contemplated. In some embodiments, the vector is preferably an adenovirus vector. In other embodiments, the vector is preferably an adeno-associated virus vector. In still further embodiments, the vector is a gutted adenovirus vector which contains no adenovirus transcriptional elements. In still other embodiments, the vector is simply naled plasmid DNA. The present invention is not limited by the location of the nucleic acid within the transfected myocyte. In some embodiments, the nucleic acid is incorporated into the genome of the host cell, while in other embodiments the nucleic acid is expressed in the cytoplasm or nucleoplasm of the host cell.

DESCRIPTION OF THE DRAWINGS

FIG. 8A and FIG. 8B project the cDNA sequences for rat, mouse and human α-parvalbumin.

DEFINITIONS

To facilitate understanding of the invention, a number of terms are defined below.

The term "myocyte" refers to muscle cells that are characterized by containing myosin. The term "cardiac myocyte" refers to cells containing myosin which are located in or isolated from the myocardium.

Figure 7:
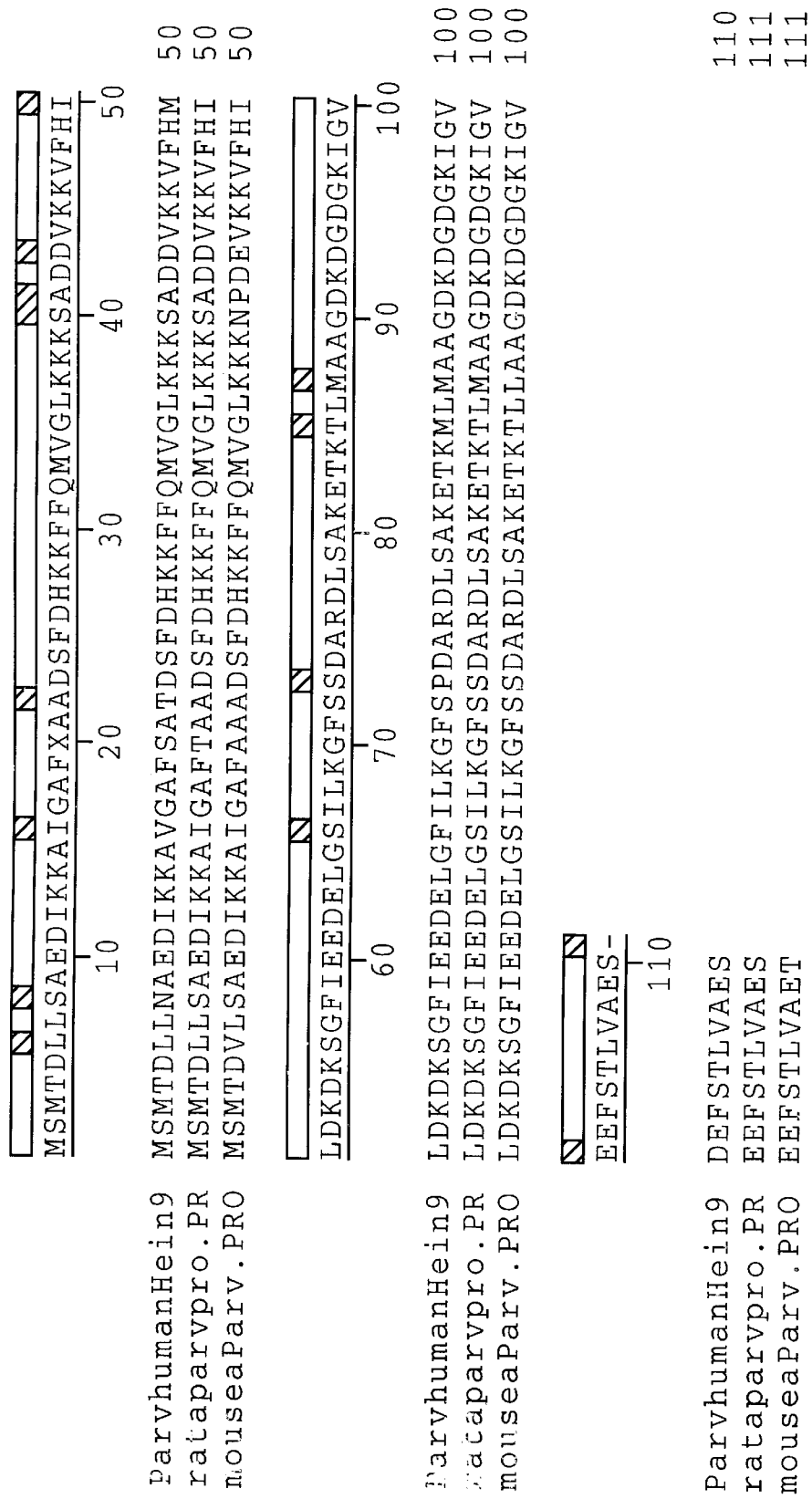
FIG. 7. Highly conserved amino acid sequence alignment for human (SEQ ID NO:4), rat (SEQ ID NO:5) and mouse (SEQ ID NO:6) α-parvalbumins.

The term "calcium binding protein" refers to any protein that has affinity for $Ca^{2+}$. Calcium binding proteins include, but are not limited to, troponin, calmodulin, and the EF-hand family of calcium binding proteins (e.g., parvalbumin, see FIGS. 7, 8A and 8B for amino acid and nucleic acid sequences).

The term "in vitro culture" refers to the propagation of cellular material outside of its natural environment.

The term "intracellular concentration," when used in reference to a protein or calcium ions, refers to the amount of protein or calcium ions in a cell.

The term "rate of sarcomere relaxation" refers to the rate at which sarcomeres re-lengthen after exposure to a stimulus which causes contraction, and is calculated as $-dl/dt$ where l is the change in length and t is time. The rate of sarcomere relaxation can be determined by laser diffraction studies.

The term "rate of isovolumic relaxation" refers to the time between closing of the aortic valve and the subsequent opening of the mitral valve.

The term "drug" refers to any compound or material that can cause or alter a biological response or is suspected of being able to cause or alter a biological response. Examples of drugs include, but are not limited to, organic molecules, inorganic molecules, peptides, proteins, RNA and DNA.

The term "gene" refers to a nucleic acid (e.g., DNA) sequence that comprises coding sequences necessary for the production of a polypeptide (e.g., parvalbumin) or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene, including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' non-translated sequences. The sequences that are located 3' or downstream of the coding region and that are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "parvalbumin gene" refers to the full-length parvalbumin nucleotide sequence (e.g., contained in SEQ ID NO:1). However, it is also intended that the term encompass fragments of the parvalbumin sequence, as well as other domains (e.g., the calcium binding domain) within the full-length parvalbumin nucleotide sequence. Furthermore, the terms "parvalbumin nucleotide sequence" or "parvalbumin polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "exogenous," when used in relation to a protein, gene, nucleic acid, or polynucleotide in a cell or organism, refers to a protein, gene, nucleic acid, or polynucleotide which has been introduced into the cell or organism by artificial or natural means. The exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript.

Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.5% SDS, 5×Denhardt's reagent and 100 μml denatured salmon sperm DNA followed by washing in a solution comprising 0.1× SSPE, 1.0% SDS at 42° C. when a probe of about 500, nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 500 nucleotides in length is employed. "Low stringency conditions" comprise conditions equivalent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4, with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.). Under "high stringency" conditions, nucleic acid base pairing will occur only between nucleic acid fragments that have a high frequency of complementary base sequences (e.g., hybridization under "high stringency" conditions may occur between homologs with about 85–100% identity, preferably about 70–100% identity).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1, wherein cDNA 2, contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the terms "restriction endonucleases" and "restriction enzymes" refer to bacterial enzymes, each of which cut double-stranded DNA at or near a specific nucleotide sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding parvalbumin, includes, by way of example, such nucleic acid in cells ordinarily expressing parvalbumin where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, TGA).

The term "recombinant DNA molecule" as used herein refers to a DNA molecule that is comprised of segments of DNA joined together by means of molecular biological techniques.

As used herein, the term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, N.Y., pp 9.31–9.58, [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al, supra, pp 7.39–7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign gene that is placed into an organism by introducing the foreign gene into cells, including but not limited to newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to one type of recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing mRNA-specific signal observed on Northern blots).

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding parvalbumin (e.g., SEQ ID NO:1) or fragments thereof may be employed as hybridization probes. In this case, the parvalbumin-encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that is a candidate for use to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the regulation of sarcomere re-lengthening.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

DESCRIPTION OF THE INVENTION

The present invention relates to the overexpression of a calcium binding protein in cardiac myocytes in vivo and in vitro, and in particular, to the correction of diastolic dysfunction. Diastolic dysfunction is a serious clinical problem for which no adequate treatment currently exists. Relaxation in striated muscle requires the rapid and efficient removal of $Ca^{2+}$ from the cytoplasm and into the sarcoplasmic reticulum. In normal cardiac muscle, $Ca^{2+}$ removal is primarily accomplished through the action of the sarcoplasmic reticulum (SR) $Ca^{2+}$ pump (Morgan, New Engl. J. Med. 325:625 [1991]). In fast-twitch skeletal muscle the SR pump is supplemented by the delayed $Ca^{2+}$ buffering capacity of parvalbumin. Parvalbumin (PV), a member of the EF-hand family of $Ca^{2+}$ binding proteins, has been shown to be correlated with increases in the rate of relaxation in fast skeletal muscle by acting as a delayed $Ca^{2+}$ sink (Hou et al., J. Physiol. 441:285–304, [1992]; Lännergren et al., J. Physiol. 463:123–140[1993]; Müntener et al., PNAS 92:6504–6508, [1995]).

The present invention utilizes gene therapy approaches to deliver and express PV calcium binding proteins (e.g., parvalbumin) in myocytes. Using these methods, expression of calcium binding proteins from exogenous nucleic acids was found to increase the rate of relaxation in cardiac myocytes from both normal and diseased (i.e., hypothyroid) rat hearts. Consequently, calcium binding protein expression in cardiac tissue represents an important new technology for the treatment of diastolic dysfunction in patients with heart failure. Additionally, this technology demonstrates that in vitro studies of parvalbumin expressing cardiac myocytes provide a new in vitro screen for the development and testing of novel cardioactive drugs and therapeutics.

A. Nucleic Acids Encoding Calcium Binding Proteins

The present invention contemplates the use of nucleic acids encoding calcium binding proteins to treat heart failure. The present invention is not limited to the use of nucleic acid encoding any particular calcium binding protein. Indeed, the use of a variety of calcium binding proteins is contemplated. Calcium binding proteins which find use in the present invention include, but are not limited to members of the EF-hand family of proteins (e.g., parvalbumin), troponin, and calmodulin. In some preferred embodiments, the calcium binding protein nucleic acid is selected from human parvalbumin (SEQ ID NO:1), rat parvalbumin (SEQ ID NO:2), and mouse parvalbumin (SEQ ID NO: 3). In other preferred embodiments, nucleic acids which bind to SEQ ID NOs:1–3 under conditions of medium to high stringency are preferably utilized. In still further embodiments, it is contemplated that fragments or portions of the calcium binding proteins encoded by SEQ ID NOs:1–3 which retain calcium binding activity are used.

B. Delivery of Calcium Binding Proteins to Cardiac Myocytes

The present invention contemplates the delivery of exogenous nucleic acids encoding calcium binding proteins to cardiac myocytes via vectors. The present invention is not limited to any particular vector. Indeed, a variety of vectors may be used to deliver the nucleic acids.

In preferred embodiments, the nucleic acid encoding a calcium binding protein is delivered via an adenovirus vector. (See e.g., Westfall et al., Meth. Cell Biol. 32:307–322 [1998]). In some embodiments, recombinant adenovirus vectors are constructed by homologous recombination of a shuttle vector containing a nucleic acid encoding a calcium binding protein and the full-length adenovirus DNA following co-transfection into a human embryonic kidney (i.e., HEK 293) cell line. In some embodiments, the full-length adenovirus DNA is provided from pJM17 which is a 0–100 map unit (m.u.) derivative of adenovirus serotype (Ad5) that contains a partial deletion in the E3 region and a 4.3-kb pBRX insert at 3.7 m.u. (See e.g., Graham and Prevec, Manipulation of Adenovirus Vectors, in *Gene Transfer and Expression Protocols*, E. J. Murray ed., Humana, Clifton, N.J. [1991]; and Becker et al., Use of Recombinant Adenovirus for Metabolic Engineering of Mammalian Cells, in *Methods in Cell Biology*, Vol 43 M. G. Roth ed., Academic Press, N.Y. [1994]). In some particularly preferred embodiments, the shuttle vector comprises 0–1 m.u. and 9–16 m.u. of the Ad5 genome flanking an expression cassette containing the nucleic acid encoding a calcium binding protein. In some embodiments, homologous recombination results in the replacement of the pBRX insert and E1 region, making the recombinant adenovirus capable of being packaged but replication defective.

In other embodiments, the nucleic acid encoding a calcium binding protein is delivered to myocytes via an adeno-associated vector (AAV). In some particularly preferred embodiments, the AAV vector integrates into the genome of the cardiac myocyte. A number of AAV vectors which have been developed for gene therapy are useful in the present invention (See e.g., U.S. Pat. Nos. 5,173,414; 5,139,941; and 5,843,742; PCT publications WO92/01070 and WO93/03769; Lebkowski et al., Mol. Cell. Biol. 8:3988–3996 [1988]; Carter, Curr. Opin. Biotech. 3:533–39, [1992]; Muzyczka, Curr. Top, Microbiol. Immunol. 158:97–129, [1994]; Kotin, Human Gene Ther. 5:793–801, [1994]; Shelling and Smith, Gene Ther. 1:165–69, [1994]; Zhou et al., J. Exp. Med. 179:1867–1875, [1994]; and Ferrari et al., Nature Med. 3(11):1295–97, [1997], each of which is incorporated herein by reference).

In still other embodiments, the nucleic acid encoding a calcium binding protein is delivered via a liposome or naked DNA plasmids. In some particularly preferred embodiments, the liposome is a cationic liposome (See e.g., U.S. Pat. Nos. 5,908,777 and 5,676,954 each incorporated herein by reference; Hug and Sleight, Biochim. Biophys. Acta. 1097:1–17, [1991]; Straubinger et al., in Methods of Enzymology, Vol. 101 pp. 512–527 [1993]; Felgner et al., Nature 337:387–388, [1989]; and Felgner et al., PNAS (1987) 84:7413–7416) [1987]). An example of a commercially available cationic liposome carrier useful in the present invention is LIPOFECTIN™ (Bethesda Research Laboratories Life Technologies, Inc., Gaithersburg Md.).

In some preferred embodiments of the present invention, the vector further includes a suitable promoter and enhancer, and also any necessary ribosome binding sites, polyadenylation site, splice donor and acceptor sites, transcriptional termination sequences, and 5' flanking nontranscribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (e.g., promoter) to direct mRNA synthesis. In some embodiments, the promoter is preferably the cytomegalovirus (CMV) promoter. In other embodiments, a cardiac specific promoter (e.g., α-MyHC and β-MyHC promoter (See e.g., Palermo et al., Circul. Res. 78(3):504–509, [1996]) is utilized. Other promoters useful in the present invention include, but are not limited to, the LTR or SV40 promoter, the *E. coli*. lac or trp, the phage lambda $P_L$ and $P_R$, T3 and T7 promoters, HSV thymidine kinase, and mouse metallothionein-I promoters and other promoters known to control expression of genes in prokaryotic or eukaryotic cells or their viruses. In other embodiments of the present invention, recombinant expression vectors include selectable markers permitting transformation of the host cell (e.g. dihydrofolate reductase or neomycin resistance for eukaryotic cell culture).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin (i.e., 100 to 270 bp), a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector includes appropriate sequences for amplifying expression.

C. Heart Failure Therapy with Calcium Binding Proteins

The present invention contemplates the treatment of diastolic dysfunction and associated heart failure through the expression in cardiac myocytes of calcium binding proteins from exogenous nucleic acids. The diastole is the period of isovolumic relaxation after aortic valve closure through mitral valve opening and the period of left ventricular filling after mitral valve opening until mitral valve closing. Heart failure due to diastolic dysfunction occurs when the left ventricle fails to receive blood during diastole at low filling pressures (See e.g., Grossman, Circulation 81(Suppl. III):1–7, [1990]; Lorell, Annu. Rev. Med. 42:411–36, [1991]). Many patients with diastolic heart failure have slowed myocardial relaxation, an important contributing factor to the elevation of diastolic pressure and to the slowing of ventricular filling in some disease states.

Without limiting the invention to any particular mechanism, it is believed that the subcellular control of contraction-relaxation involves the ATP dependent regulation of cytosolic $Ca^{2+}$ levels. During systole, the sarcolemma is depolarized, and $Ca^{2+}$ entry via slow $Ca^{2+}$ channels triggers the release of $Ca^{2+}$ from terminal cisternae in the sarcoplasmic reticulum. The increase in $Ca^{2+}$ concentration results in the binding of $Ca^{2+}$ to the troponin-C subunit of troponin. This causes a conformational change in tropomyosin, which uncovers actin molecules and allows crossbridge attachment and contraction of the sarcomeres. The reduction of systolic force requires the rapid reduction of $Ca^{2+}$ to its basal level. Reduction in $Ca^{2+}$ is facilitated by the ATP-dependent $Ca^{2+}$ pump in the sarcoplasmic reticulum. The reduction in $Ca^{2+}$ favors the disassociation of $Ca^{2+}$ from troponin. ATP binds to the contractile proteins, resulting in detachment of the actin-myosin crossbridges.

It is not intended that the present invention be limited to a particular mechanism of action. Indeed, an understanding of the mechanism is not necessary to make and use the present invention. However, it is contemplated that the expression or overexpression of calcium binding proteins in cardiac myocytes creates a "calcium sink" for the removal of free intracellular calcium in the cardiac myocytes. Expression of the calcium binding proteins causes a faster decay in the intracellular calcium transient that governs the contractile event, as well as a faster mechanical relaxation in cardiac myocytes from normal and diseased hearts. Expression of parvalbumin in both in vitro and in vivo in cardiac myocytes increases the rate of relaxation of the myocardium. It is believed that this parvalbumin-mediated increase in the rate of relaxation will increase filling of the left ventricle during diastole, causing relief from the symptoms of diastolic dysfunction.

Accordingly, the present invention provides methods for treating heart failure due to diastolic dysfunction. In some embodiments of the present invention, the vectors described above are used to deliver exogenous nucleic acid encoding a calcium binding protein to cardiac myocytes (i.e., transfect the cardiac myocytes). In some embodiments, the vectors (e.g., liposome vectors or AAV vectors) are administered directly to the left ventricular wall of the heart. In preferred embodiments, an adenovirus vector containing a expression cassette encoding a calcium binding protein (e.g., SEQ ID NOS:1–3) is injected into the left ventricle. In some preferred embodiments, the calcium binding protein is expressed from the nucleic acid so that intracellular levels of the calcium binding protein are greater than in wild-type (i.e., non-transfected) cardiac myocytes. In particularly preferred embodiments, the rate of isovolumic relaxation of the left ventricle in transfected animals or humans with symptoms of diastolic dysfunction is faster than is observed in non-transfected humans or animals suffering from diastolic dysfuction. The rate of isovolumic relaxation is measured by M-mode and doppler echocardiography. The rate of isovolumic relaxation refers to the time between closing of the aortic valve and reopening of the mitral valve.

D. Drug Screens

It is also contemplated that the cardiac myocytes comprising an exogenous nucleic acid encoding a calcium binding protein are used in a variety of drug screening assays. In some embodiments, the cardiac myocytes are used as a control for the screening of potential cardioactive reagents and therapeutics. In some embodiments, cells expressing exogenous calcium binding proteins are used as a functional guide of robust improvement in cardiac relaxation kinetics. The use of cardiac myocytes expressing exogenous parvalbumin as controls makes it possible to rapidly screen and select drugs and therapeutics which mimic the effectiveness of parvalbumin in vivo and in vitro. In other embodiments, materials are identified which potentially compound diastolic dysfunction.

In some preferred embodiments, cardiac myocytes expressing exogenous parvalbumin (e.g., transfected cardiac myocytes) and wild-type cardiac myocytes are provided. In some embodiments, the transfected and wild-type cardiac myocytes are then exposed in vitro to a material (e.g., drug or therapeutic agent) suspected of having a cardioactive effect. In some preferred embodiments, the rate of relaxation of the sarcomeres in the transfected and wild-type cardiac myocytes is then assayed. In some preferred embodiments, the rate of sarcomere relaxation is assayed by laser diffraction. The myocytes are electrically stimulated and times are calculated for stimulation to maximum shortening and maximum shortening to ½ re-lengthening. The rate of relaxation is calculated as $-dl/dt$ where l is the change in length and t is time. In some embodiments, materials which increase the rate of sarcomere relaxation in the wild-type myocytes to levels comparable to those observed in non-treated, transfected myocytes are chosen for further in vivo testing for the treatment of heart failure due to diastolic dysfunction. In other embodiments, materials which decrease the rate of sarcomere relaxation in transfected or wild-type cardiac myocytes are identified as being materials which potentially cause or compound diastolic dysfunction.

In other preferred embodiments, animals expressing exogenous parvalbumin (e.g., transfected animals) in their cardiac myocytes and wild-type animals are provided so that the cardioactivity of materials may be assayed in vivo. In some embodiments, materials suspected of having a cardioactive effect are administered to the animals. In some particularly preferred embodiments, these materials have been identified in the in vitro screen described above. In some embodiments, the rate of isovolumic relaxation is calculated in treated and non-treated animals. In some embodiments, materials which cause an increase in the rate of isovolumic expansion comparable to that seen in non-treated, transfected animals are identified as candidates to treat heart failure due to diastolic dysfunction. In other embodiments, materials which decrease the rate of isovolumic relaxation in wild-type or transfected animals are identified as being materials which potentially cause or compound diastolic dysfunction.

EXPERIMENTAL

The following examples are provided in order to demonstrate and further illustrate certain preferred embodiments and aspects of the present invention and are not to be read as limiting the scope thereof.

Example 1

Vector Construction

This example describes the construction of recombinant adenovirus vectors containing a parvalbumin insert (See e.g., Westfall et al., Meth. Cell Biol. 32:307–322, [1998], incorporated herein by reference). Recombinant adenovirus vectors are constructed by co-transfecting the pJM17 plasmid and a shuttle vector plasmid into HEK 293 cells with calcium phosphate. The pJM17 plasmid is a 0–100 map unit (m.u.) derivative of adenovirus serotype 5 (Ad5) that contains a partial deletion in the E3 region and a 4.3-kb pBRX insert at 3.7 m.u. This insert allows replication of the plasmid in bacteria but makes the viral genome too large to be packaged within the virus capsid. The shuttle plasmid contains 0–1 m.u. and 9–16 m.u. of the Ad5 genome, flanking an expression cassette containing the cytomegalovirus (CMV) promoter, the coding sequence of interest (e.g., SEQ ID NO:1, SEQ ID NO:2, or SEQ ID NO: 3), and the SV40 polyadenylation signal. Following homologous recombination, the expression cassette replaces the pBRX insert and the E1 region of the genome (1–9 m.u.) in pJM17 thus making the recombinant adenovirus capable of being packaged but replication defective. The HEK 293 cell line is Ad 5 transformed and expresses the E1 region (1–11.3 m.u.) in trans, which allows for replication of recombinant adenovirus. Methods for maintaining HEK 293 cells, preparing plasmids, and constructing recombinant adenovirus are described below.

Maintenance of HEK 293 Cells: HEK 293 cells are used for construction and plaque purification of recombinant adenovirus as well as for preparation of virus for infection of ventricular myocytes. The HEK 293 cells are maintained on 60-mm culture dishes in DMEM +10% FBS+P/S and are split when they are 85% confluent. To split the cells, media is aspirated from the cells and 1–1.5 ml 0.05% trypsin/0.53 mM EDTA are then added. Once the cells begin to lift off the plate, 5 ml DMEM+10% FBS+P/S are added to the culture dish. The trypsinized cells are then transferred into 50-ml tubes and briefly centrifuged at 1000 rpm in a Beckman GPR centrifuge. To have cells at 80% confluency in 2 days, one dish of 90%–100% confluent cells should be split 1:2 or 1:3. To have cells about 80% confluent in 3–4 days, cells should be split 1:5 or 1:6. If the cells are plated too sparsely, they will not proliferate.

Co-transfection of HEK 293 Cells: Co-transfection is carried out using HEK 293 cells at 80–90% confluency. Cells are maintained in 60-mm dishes with DMEM+10% FBS+P/S and fresh media is added ~24 hr prior to transfection. The adenovirus DNA (e.g. pJM17) and the shuttle plasmid containing the expression cassette are co-transfected into HEK 293 cells using calcium precipitation. This reaction is started by adding 10 $\mu$g of the shuttle vector and 10 $\mu$g of pJM17 to 500 $\mu$l of 2×HBS and then adding water to a volume of 937.5 $\mu$l in a sterile 1.5 ml microfuge tube. The tube is inverted several times to mix the contents, 62.5 $\mu$l of 2M $CaCl_2$ is added, and the contents mixed again. The precipitate is allowed to form at room temperature for 45–60 min. For transfection, 500 $\mu$l of the $CaPO_4$ precipitate is added dropwise to each 60-mm dish of HEK 293 cells. The cells are incubated at 37° C. for 4–5 hr in a 95% $O_2$, 5% $CO_2$ incubator. The cloudy and turbid media is removed by aspiration, then the cells are washed with PBS. Four ml DMEM+10% FBS+P/S medium is then added.

The medium is exchanged with 3 ml fresh medium the next day to remove dead cells. Then, 2 ml of medium is added each day for 3–4 days without removing the old medium. Plaques begin appearing 7–10 days following transfection and the full cytopathic effect (CPE) is seen within 3–5 days of plaque appearance. The cells are collected in 15 ml polypropylene tubes after full CPE is evident. The cell suspension is exposed to three cycles of freezing and thawing to lyse intact cells and release the virus. The suspension is centrifuged at 2500 rpm for 10 min to separate cellular debris from the virus. The supernatant, which contains the virus, is aliquoted and stored at −20° C.

Construction of Vector with Human Paravalbumin (PV) Insert: Briefly, pJM17 and a shuttle plasmid containing the α-PV expression cassette were co-transfected into HEK 293 cells using calcium phosphate precipitation. The shuttle plasmid, PCA4 was digested with restriction enzymes Xba I and Hind III to subclone in the Xba I and Hind III digested full length, human a-PV cDNA (Genbank Accession X63070 Fohr et al., Eur. J. Biochem. 21593):719–27, [1993]). Homologous recombination occurred in HEK 293 cells, and plaques began appearing within 7–10 days of co-transfection. Cells were collected after full cytopathic effect became evident, 3–5 days after plaque appearance, virus was released by three cycles of freezing and thawing, and virus was collected by centrifuging at 2500 RPM for 10 min. and collecting the supernatant which contained the viral stock.

Plaque assays were performed to obtain clonal recombinant adenovirus stocks. Briefly, serial dilutions of the viral stock were prepared and used to infect HEK 293 cells. After infection, the dishes were overlayed with MEM/agar and incubated for 7–10 days. Individual plaques were collected by transferring agar plugs containing well-isolated plaques to separate cryotubes containing DMEM+10% FBS+P/S. Plaques were expanded by infecting HEK 293 cells and collecting the cell lysate after full cytopathic effect was evident as described above. Plaques were screened by Southern blot analysis to identify recombinant adenovirus containing the a-PV cDNA.

Plaque-purified recombinant adenovirus stocks were amplified by large scale grow-ups and CsCl purification. Thirty 150 mm dishes of HEK 293 cells were infected with the clonal stock of recombinant adenovirus. After cytopathic effect was evident, cells were collected, centrifuged to pellet the cells, resuspended in 10 mM Tris-Cl (pH 8.0), lysed by freezing and thawing, and centrifuged to pellet the cellular debris. The supernatant was treated with RNase A and DNase I (50 mg/ml solutions), centrifuged, and the supernatant was transferred to a clean tube. The CsCl gradient was poured in Ultra-Clear centrifuge tubes and centrifuged using an SW28 rotor for 4 hr at 20,000 RPM, at 5° C. The lowest band, which contains infectious recombinant adenovirus, was recovered and transferred to a Quick-Seal tube. The tube was filled with 1.34 g/ml CsCl and centrifuged using an NVTi65 rotor overnight at 63,000 RPM, at 5° C. The band was recovered and dialyzed against PBS for 1–2 hr. then against PBS+10% glycerol for overnight. The purified recombinant virus stock was then diluted and/or aliquoted for storage at 80° C.

Example 2

Parvalbumin Expression in Cardiac Myocytes

This example describes the expression of parvalbumin in isolated myocytes. Intact myocytes were isolated from normal and hypothyroid female Sprague Dawley rats by enzymatic digestion as described previously (Westfall, et al., supra). Rats were made hypothyroid by adding 0.6% propylthiouracil to the drinking water for a minimum of 4 weeks prior to myocyte isolation. Myocytes were isolated by removing the heart from an anesthetized rat and perfusing the heart with Kreb's Henseleit Buffer (KHB)+1 mM $CaCl_2$ for 5 minutes on a modified Langendorff perfusion apparatus. The heart was then perfused with $Ca^{2+}$-free KHB for 5 minutes followed by addition of collagenase (0.5 mg/ml) and hyaluronidase (0.2 mg/ml) for 15 minutes. The ventricles were then minced and serially digested for 2×10 minutes and 2×15 minutes in the enzyme solution. The last two digests were collected by brief centrifugation and resuspended in KHB+1 mM $CaCl_2$+2% BSA. The solution was titrated to 1.8 mM $Ca^{2+}$ by three additions of 100 mM $CaCl_2$ over 15 minutes. The myocytes were plated on laminin coated glass coverslips in DMEM+5% serum at $1 \times 10^5$ cells/ml for 2 hours. The myocytes were then incubated with adenovirus at 500 MOI (pfu/cell) diluted in serum-free DMEM, P/S. Myocytes were studied on day 4 following incubation.

Western blot analysis was performed as described (See Westfall et al., supra). For indirect immunofluorescence, cultured myocytes were fixed in 3% paraformaldehyde/PBS for 30 minutes, washed and incubated in PBS+50 mM $NH_4Cl$ for 30 minutes. Primary (PARV19, 1:500 Sigma) and secondary (anti-mouse IgG-Texas Red, 1:100 Molecular Probes) antibodies were diluted in 2% goat serum in PBS+ 0.5% TRITON-X 100. Non-specific binding was blocked by incubation in 20% NGS/PBS +0.5% TRITON-X 100 before adding antibody. To visualize actin, FITC-phalloidin was dissolved in DMSO and applied to myocytes for 20 minutes at a dilution of 1:1000. Samples were examined on a Nikon Diaphot 200 microscope outfitted with a Noran confocal laser imaging system.

The PV expression on day 4 from a series of AdαPV incubation levels indicated that incubation with 500 moi AdαPV produced an optimal expression of PV on day 4 of culture. Therefore, isolated myocytes were incubated at 500 moi AdαPV and studied on day 4. Incubation with 500 moi AdLacZ was used as a control for the effects of adenoviral-mediated gene transfer. Western blots indicated that transfected myocytes express significant amounts of parvalbumin after 4 days in culture (data not shown). Other proteins were unchanged.

Example 3

$Ca^{2+}$ Transients

Figure 3:
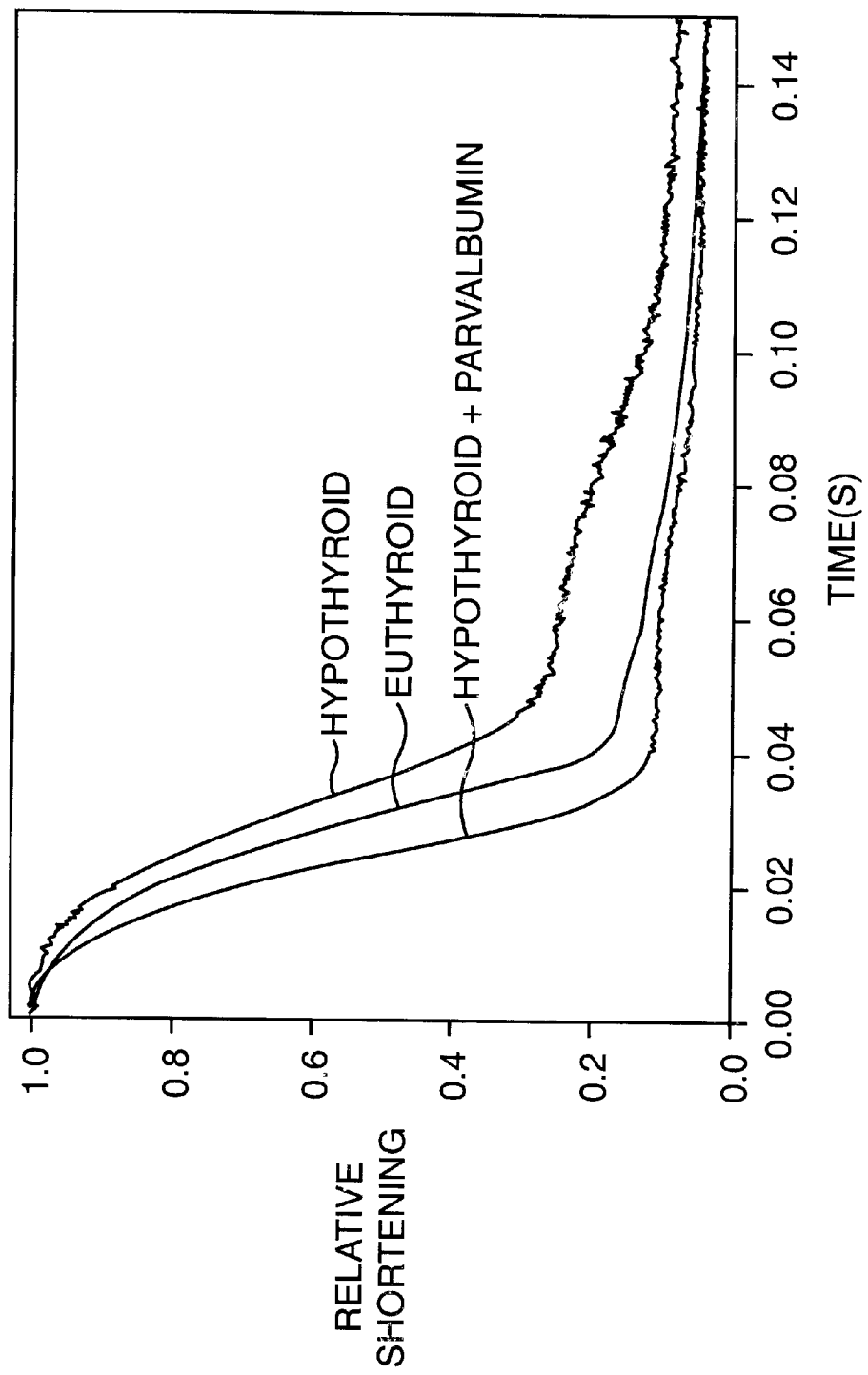
FIG. 3. Parvalbumin expression fully corrects the diastolic dysfunction in cardiac myocytes isolated from an animal model (i.e., hypothyroid model) of human heart failure.

In this example, the fluorescent indicator fluo-3 was used to monitor $Ca^{2+}$ transients induced by electrical stimulation in transfected myocytes (See FIG. 3). $Ca^{2+}$ measurements were made in a Krebs-Henselait Buffer (KHB) containing 5 mM glutathione, 1.8 mM $CaCl_2$, 118 mM NaCl, 4.8 mM KCl, 25 mM HEPES, 1.2 mM $KH_2PO_4$, 1.2 mM $MgSO_4$ and 11 mM glucose. Fluo-3 AM solutions were made fresh by dissolving 50 µg fluo-3 AM (Molecular Probes) in 10 µl DMSO and diluting to 5 µM in KHB. Coverslips on which the myocytes had been plated were removed from the stimulation chamber and mounted on a heated microscope stage in a custom made chamber similar to that used for the laser diffraction studies. After mounting, the coverslip was washed briefly with KHB. This solution was subsequently replaced with the fluo-3 AM solution for loading at 37° C. Myocytes were loaded with fluo-3 AM for 10 minutes, the fluo-3 AM solution was replaced by the KHB solution and an additional 20 minutes was allowed for de-esterification. Fluorescence was stimulated by an argon laser at 488 nm. Images were collected at 480 Hz on a Noran confocal imaging system.

The fluorescence intensity was averaged over the entire myocyte in each image and plotted vs time. The intensity vs time plot from three stimulations were averaged for each myocyte studied. Estimates of the $[Ca^{2+}]_i$ were provided by the equation $$[Ca^{2+}]_i = KR/((K/[Ca^{2+}]_{rest}) - R + 1)$$

where R is the normalized fluorescence ($F/F_{rest}$) and K is the fluo-3 $Ca^{2+}$ affinity (See e.g., Cannell et al., Biophs. J. 67:1942–56, [1994]). A value of 1.57 µM was used for K (See e.g., Baylor and Hollingworth, J. Gen. Physiol. 112:297–316, [1998]) and $[Ca^{2+}]_{rest}$ was assumed to be 100 nM.

Figure 1:
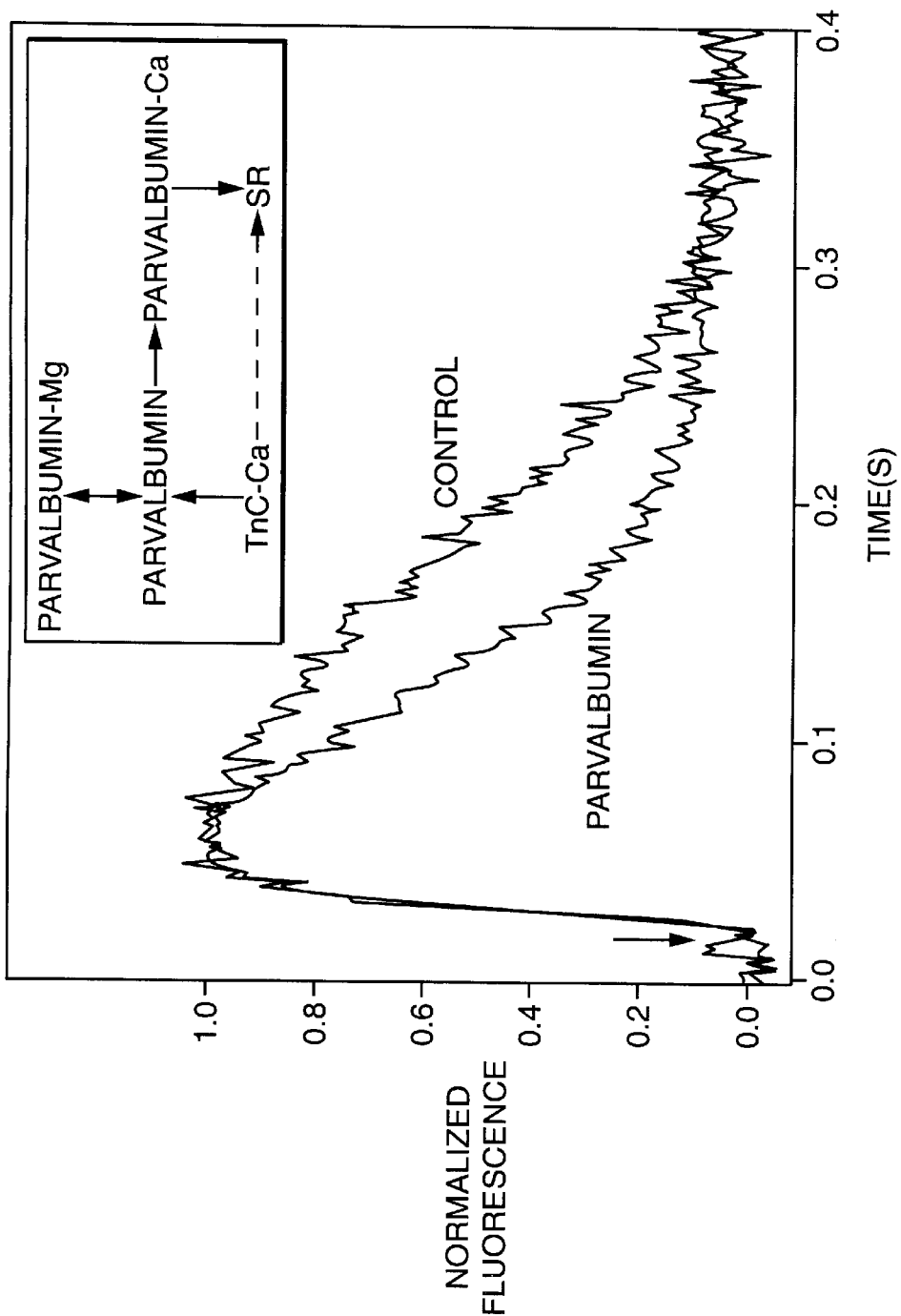
FIG. 1. Accelerated decay of intracellular calcium by ectopic parvalbumin expression in cardiac myocytes in vitro.

The effect of PV on the $Ca^{2+}$ transient was measured directly using fluo-3 to monitor changes in the intracellular $Ca^{2+}$ concentration. A typical example is shown in FIG. 1. As can be seen in FIG. 1, the rate of fluorescence decay is significantly faster in myocytes following PV gene transfer as compared with control. In contrast, lac-Z gene transfer had no significant effect on the time course of the $Ca^{2+}$ transient. To quantify this, the fluo-3 fluorescence over time was plotted and the decay phase was fit to a single exponential. Results are presented in Table I.

TABLE I

Parameters of Ca Transient as Measured by Fluo-3 Fluroescence at 37° C. in Cardiac Myocytes In Vitro

|  | $t_{FWHM}$ | N |
| --- | --- | --- |
| Control | 177.6 ± 5.4 | 18 |
| PV | 100.9 ± 8.4* | 10 |
| Lac-Z | 179.2 ± 9.0 | 13 |

*significantly different from control or lacZ (p < 0.5).

Example 4

Rate of Sarcomere Shortening and Re-Lengthening

In this example, the rate of sarcomere shortening and re-lengthening in transfected and control myocytes is analyzed. In order to retain the excitability of myocytes after several days in culture, it was necessary to electrically stimulate the myocytes in culture. Plated myocytes were placed in a stimulation chamber which consisted of a series of wells milled into a plastic slab with a glass bottom for viewing the cells on a microscope. Field stimulation was provided by platinum electrodes placed along parallel sides of the wells. Cells were stimulated in media 199 supplemented with 0.2 mg/ml BSA, 50 units/ml penicillin, 50

μg/ml streptomycin, and 5 mM glutathione. The presence of glutathione was necessary to maintain the viability of myocytes during long-term stimulation. The cells were stimulated continuously at 0.5 Hz with a 2.5 ms pulse width whose amplitude was set at a level at which >50% of the cells responded. It was necessary to replace the media every 8–12 hours to maintain cell viability. Stimulation began on the morning following myocyte isolation to allow sufficient time for cell attachment to the laminin coated coverslips.

Sarcomere length was followed using laser diffraction. A coverslip containing cultured myocytes was removed from the stimulation chamber and placed in the diffraction chamber. The diffraction chamber consisted of a temperature controlled microscope stage with an opening through which the output of a 10 mW HeNe laser was focused. The chamber was constructed such that the coverslip containing the myocytes formed the bottom of the chamber and had platinum electrodes along the sides to allow electrical stimulation of the myocytes. The output of a 10 mW HeNe laser was focused onto the coverslip using an achromatic lens to a small spot size. A myocyte was positioned in the laser beam and the first order diffraction line was focused with a cylindrical lens onto a linear position detector (LSC 5D or 30D, UDT Sensors, Inc., Hawthorne, Calif.). The output of the detector was amplified and recorded on a digital oscilloscope. The records of ten twitches from each myocyte studied were averaged for subsequent analysis. After the above protocol, the detector was removed and a screen was inserted in the beam path. The position of the first order relative to the zero order diffraction pattern on this screen was then used to estimate the initial sarcomere length and, whenever possible, the amplitude of the sarcomere length change following electrical stimulation.

Myocytes were electrically stimulated with a 5 ms square pulse and the resulting movement recorded at 5000 Hz. The time from stimulation to maximum shortening ($t_{peak}$), from maximum shortening to ½ re-lengthening ($t_{1/2}R$), and the full width of the trace at ½ of the maximum shortening length ($t_{FWHM}$) were measured from the average trace for each myocyte. In addition, the maximum rate of shortening and re-lengthening (+and −dl/dt, respectively) were calculated normalized to the maximum amplitude. One-way ANOVA with a post-hoc Tukey multiple comparison test was used to compare measurements between multiple data sets with p<0.05 indicating significance.

Figure 2:
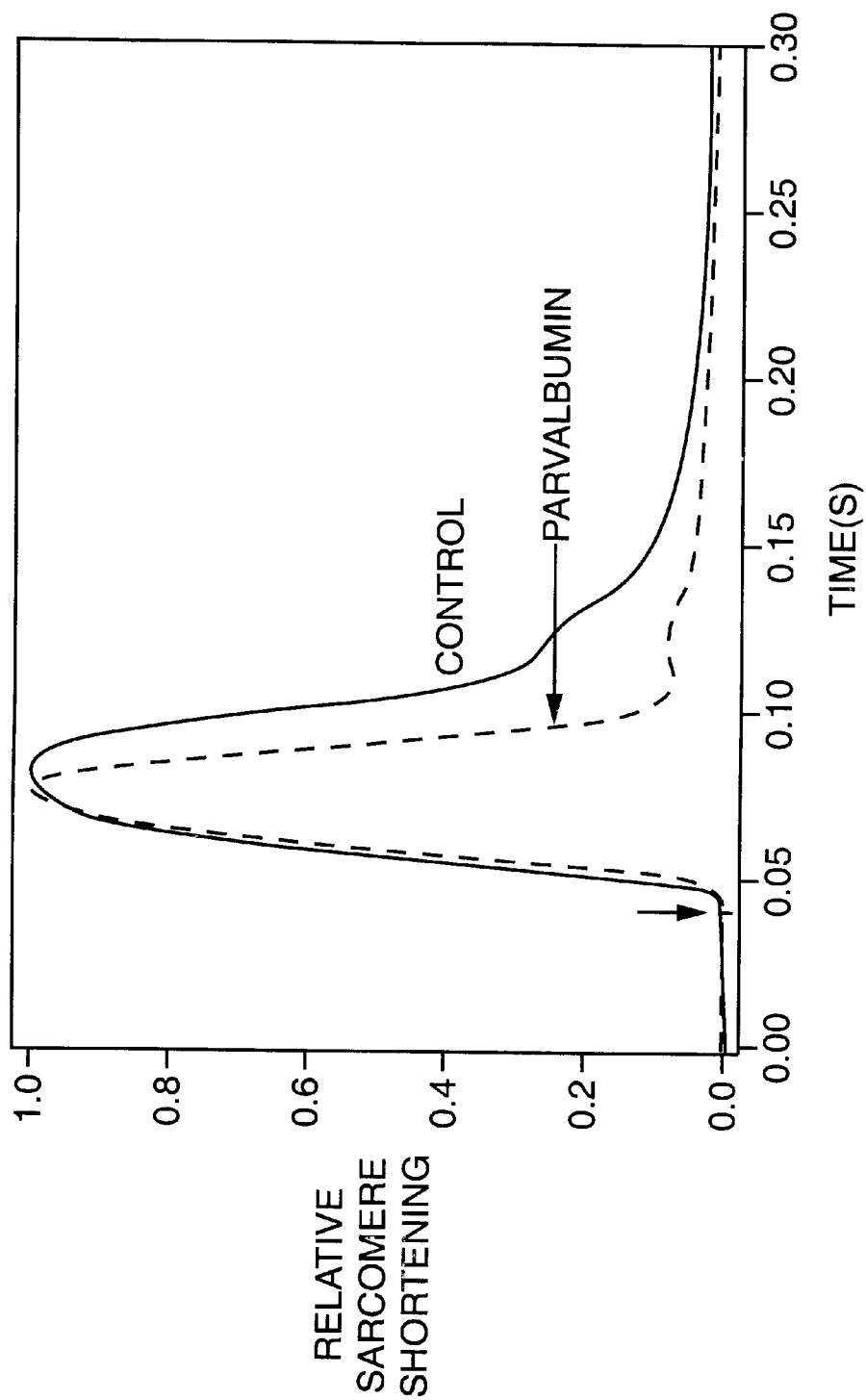
FIG. 2. Accelerated relaxation by ectopic paravalbumin expression in cardiac myocytes in vitro.

An example of the change in the first order diffraction position with stimulation is shown in FIG. 2. The time to peak shortening ($t_{peak}$), half relaxation ($t_{1/2}R$), and the width of the trace at half of the maximum amplitude ($t_{fwhm}$) were measured. In addition, the maximum rates of sarcomere shortening and re-lengthening (+and −dl/dt) were calculated. The values for these parameters are given in Table II. These results demonstrate that parvalbumin expression significantly accelerates relaxation properties of adult cardiac myocytes. Cardiac myocytes expressing PV showed a significantly faster re-lengthening than control myocytes at both 25 and 37° C. Comparison of the results with different temperatures indicates that $t_{1/2}R$ and −dl/dt become less temperature sensitive in the myocytes expressing PV. Given the relative difference in $Q_{10}$ between the SR $Ca^{2+}$ ATPase and the PV binding kinetics, this indicates that the twitch relaxation becomes dominated by $Ca^{2+}$ binding to PV instead of the SR. In addition, ectopic expression of PV in myocytes from diseased hearts (hypothyroid) was found to restore relaxation function back to control levels (See FIG. 3).

TABLE II

Parameters of Sarcomere Shortening and Re-lengthening as Measured by Laser Diffraction of Cardiac Myocytes In Vitro

|  | $t_{peak}$ (ms) | $t_{1/2R}$ (ms) | $t_{FWHM}$ (ms) | +dl/dt | −dl/dt | N |
|---|---|---|---|---|---|---|
|  |  |  | 37° C. |  |  |  |
| Control | 47.1 ± 1.7 | 27.9 ± 1.5 | 55.1 ± 2.1 | 12.51 ± 0.76 | 7.74 ± 0.52 | 48 |
| PV | 43.0 ± 2.2 | 21.1 ± 1.7* | 43.8 ± 2.8* | 12.77 ± 0.67 | 10.61 ± 0.64* | 43 |
| Lac-Z | 51.9 ± 2.0 | 34.1 ± 2.9 | 67.1 ± 3.6* | 13.47 ± 0.77 | 7.77 ± 0.75 | 32 |
|  |  |  | 25° C. |  |  |  |
| Control | 148.5 ± 5.7 | 105.7 ± 6.4 | 211.1 ± 8.7 | 5.16 ± 0.29 | 2.48 ± 0.15 | 40 |
| PV | 138.9 ± 5.4 | 61.3 ± 3.2* | 147.4 ± 6.2* | 4.58 ± 0.24 | 3.77 ± 0.18* | 45 |
| Lac-Z | 146.0 ± 7.9 | 100.9 ± 11.6 | 196.5 ± 15.0 | 4.94 ± 0.45 | 3.02 ± 0.26 | 24 |

*significantly different from control or lacZ (p < 0.5).

Example 5

Effect of In Vivo Expression of Parvalbumin from Adenoviral Vector

Figure 4:
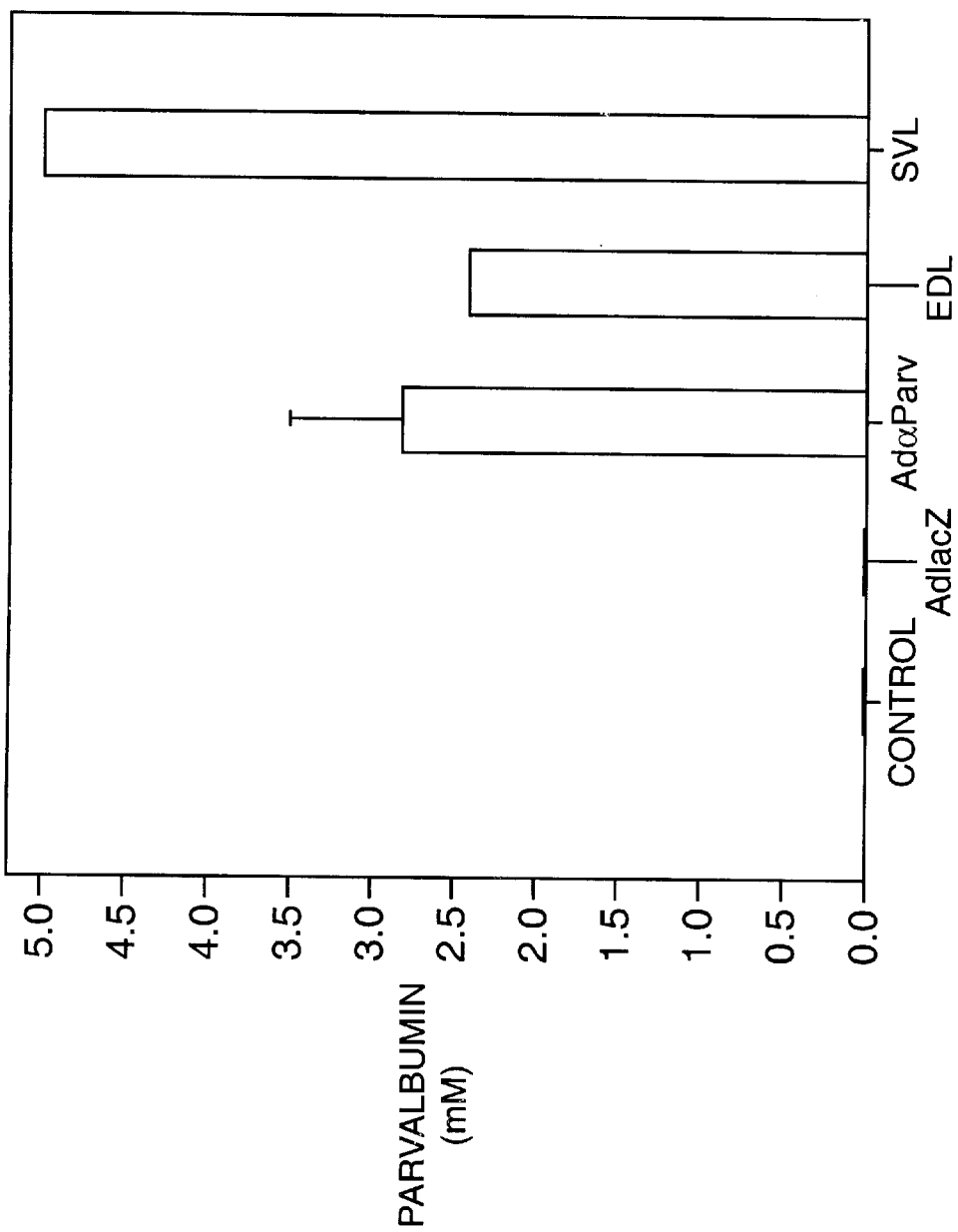
FIG. 4. Ectopic expression of parvalbumin in the rat heart in vivo. Parvalbumin expression was estimated in heart ventricular samples by comparing intensity of immunoreactive bands of heart samples with those from fast skeletal muscle positive control samples.

This example describes the effects of in vivo expression of parvalbumin in rat hearts. An adenoviral vector containing the parvalbumin expression cassette was delivered directly into the left ventricular free wall of adult female rats via a syringe. Adult female rats were sedated, intubated, placed on artificial ventilation, thoracotamized, and hearts injected with recombinant adenoviral vectors. At six days post gene transfer the hearts were removed and the left ventricular free wall isolated for detection of parvalbumin expression via Western blot analysis. There was marked ectopic parvalbumin expression in these hearts after gene transfer. Parvalbumin expression was estimated in heart left ventricular samples by comparing intensity of immunoreactive bands of heart samples with those from fast skeletal muscle positive control samples. As summarized in FIG. 4, there was marked ectopic parvalbumin expression in these hearts after gene transfer. On average, the amount of parvalbumin expression was 118% of the amount expressed in the extensor digitorium longus, a hindlimb fast twitch skeletal muscle. In other experiments, hearts where isolated, cryoprotected, thin sectioned, and immunostained for localization of parvalbumin in the heart. Results (data not shown) indicated that there was expansive expression of parvalbumin across the left ventricle, extending from the base to the apex. There was comparatively little expression detected in the right ventricle.

Figure 5:
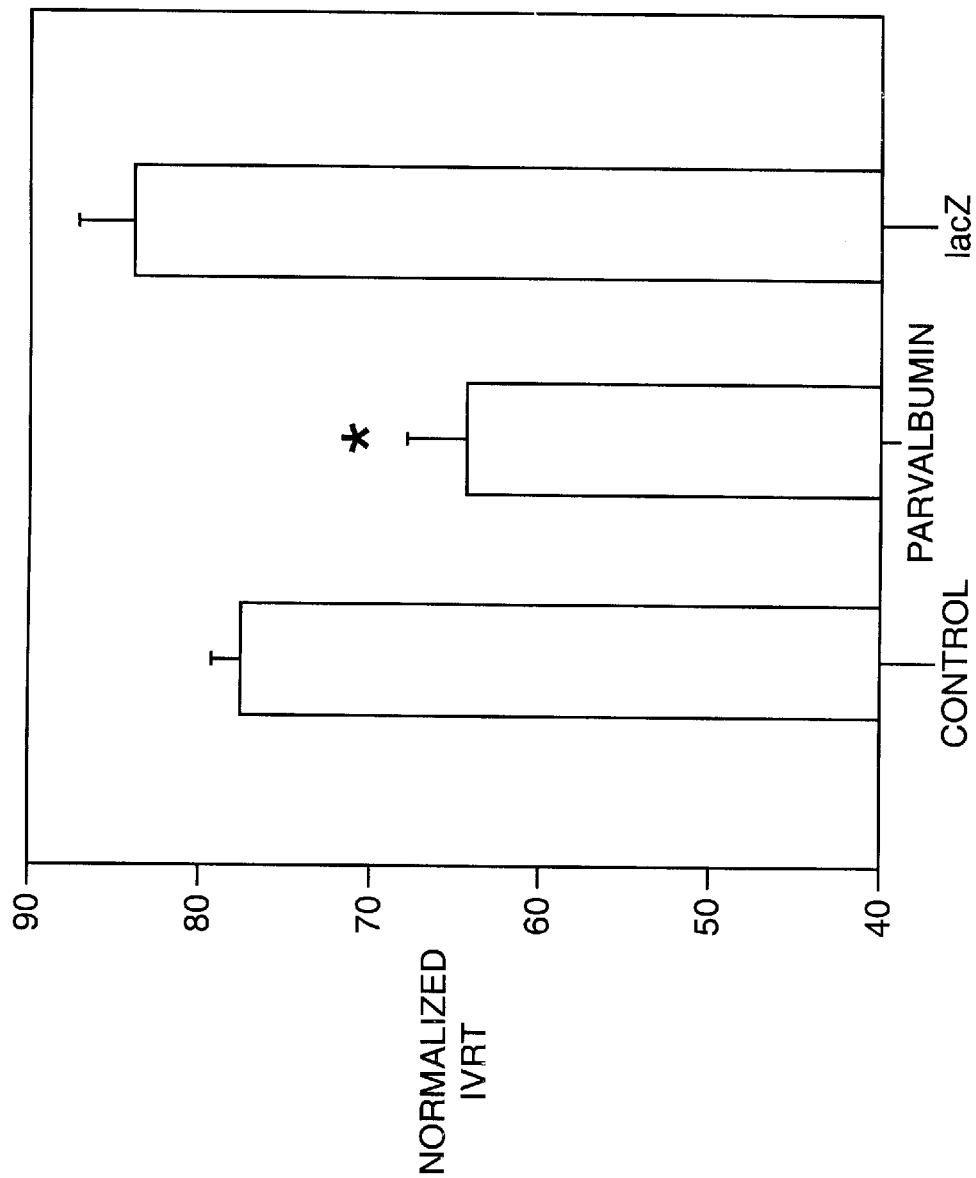
FIG. 5. Enhanced diastolic function of the heart in vivo by parvalbumin gene transfer as assessed by echocardiography. IVRT is isovolumic relaxation time normalized for heart rates. *Indicates significantly different from control ($p<0.05$) and lacZ.

Importantly, it was discovered using two different functional assays, that parvalbumin expression directly causes a significant increase in left ventricular muscle relaxation rates. In the first study, living animals were examined non-invasively by M-mode and doppler echocardiography. Results showed that the isovolumic relaxation time was significantly faster in animals treated with the parvalbumin vector compared with either sham operated controls or lacZ vector treated (FIG. 5). It was further demonstrated that a significant correlation existed (r=−0.88; P=0.0016) between the IVRT and amount of parvalbumin expression in each heart. This provides strong evidence that the hastened IVRT was due to a direct effect of parvalbumin expression.

Figure 6:
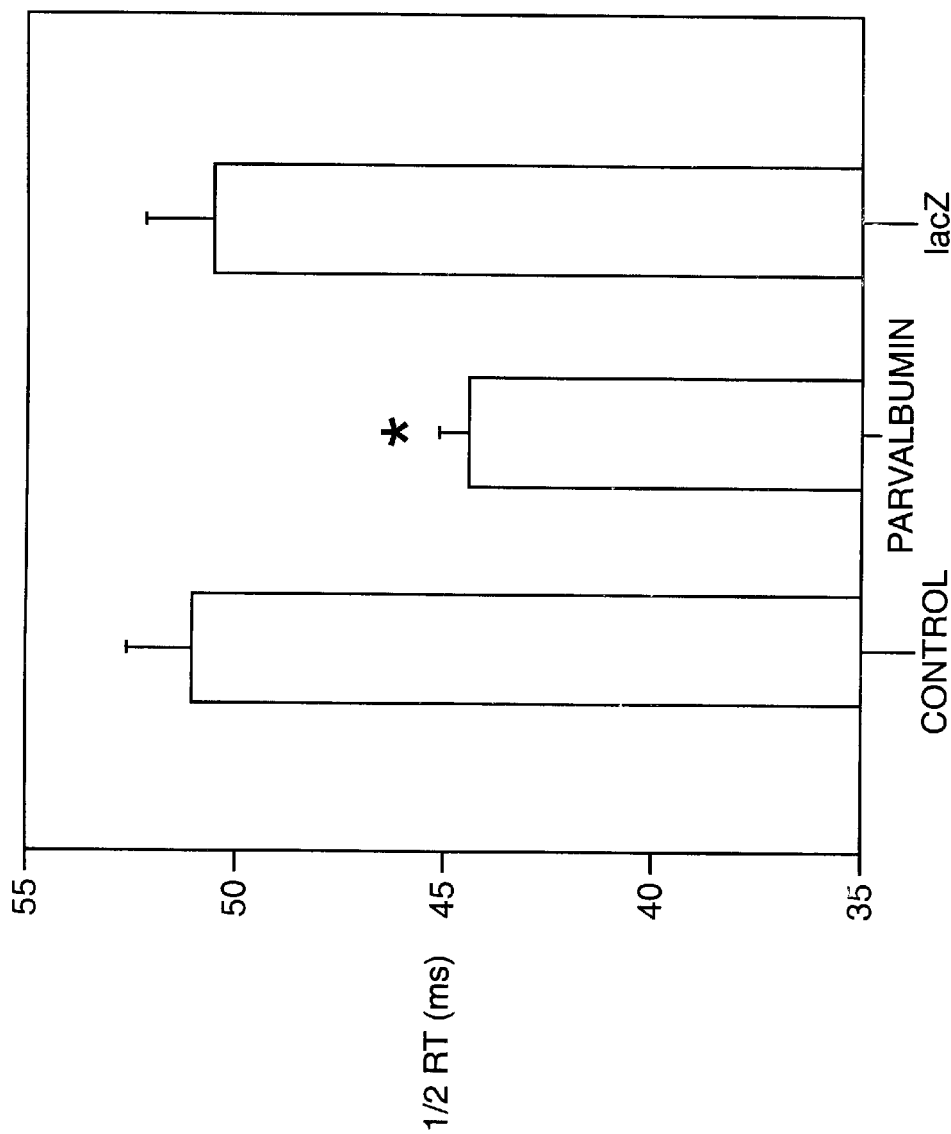
FIG. 6. Enhanced relaxation of the heart by parvalbumin gene transfer in vivo as assessed by direct measurements of left ventricular force output. Asterisks indicates significant difference ($p<0.05$ between parvalbumin treated group with sham controls and lacZ treated hearts.

In a second series of studies, whole hearts were removed from animal at day six post gene transfer, attached to a perfusion apparatus for direct recording of force relaxation kinetics. Results indicated a significant speeding of relaxation in hearts after parvalbumin gene transfer as compared with data from sham controls or lacZ treated animals (FIG. 6). These findings are the first to demonstrate that parvalbumin gene transfer and expression in the heart can directly affect diastolic functionality of the myocardium in vivo.

What should be clear from above is that the present invention provides vectors and methods for directly treating heart failure due to diastolic dysfunction. Expression of calcium binding proteins in cardiac myocytes leads to increased rates of relaxation both in vivo and in vitro with few apparent side effects.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, or related fields are intended to be within the scope of the following claims.

What is claimed is:

1. A method comprising:
   a) providing:
      i) a drug candidate and
      ii) an in vitro cultured mammalian cardiac myocyte comprising an exogenous nucleic acid encoding a calcium binding protein operatively linked to a promotor;
   b) exposing said in vitro cultured mammalian cardiac myocytes to said drug candidate; and
   c) assaying the rate of relaxation of said in vitro cultured mammalian cardiac myocytes.

2. The method of claim 1, wherein said exogenous nucleic acid is selected from SEQ ID NOs: 1–3.

3. The method of claim 1, wherein the intracellular concentration of said calcium binding protein in said in vitro cultured mammalian cardiac myocytes is greater than in vitro wild type mammalian cardiac myocytes.

* * * * *